United States Patent
Zeiss et al.

(10) Patent No.: US 7,213,598 B2
(45) Date of Patent: May 8, 2007

(54) NAVIGATION-CALIBRATING ROTATIONALLY ASYMMETRICAL MEDICAL INSTRUMENTS OR IMPLANTS

(75) Inventors: Mario Zeiss, Poing (DE); Arno Blau, Feldkirchen (DE); Rainer Birkenbach, Poing (DE); Falko Seifferth, Zorneding (DE)

(73) Assignee: BrainLAB AG, Feldkirchen (DE)

( * ) Notice: Subject to any disclaimer, the term of this patent is extended or adjusted under 35 U.S.C. 154(b) by 520 days.

(21) Appl. No.: 10/446,649

(22) Filed: May 28, 2003

(65) Prior Publication Data

US 2004/0039402 A1 Feb. 26, 2004

Related U.S. Application Data

(60) Provisional application No. 60/437,534, filed on Dec. 31, 2002.

(30) Foreign Application Priority Data

May 28, 2002 (EP) ................................. 02011600

(51) Int. Cl.
*A61B 19/00* (2006.01)
(52) U.S. Cl. .................................................... 128/897
(58) Field of Classification Search ........ 128/897–899; 606/1, 130; 73/865.9, 1.01, 1.79, 1.75
See application file for complete search history.

(56) References Cited

U.S. PATENT DOCUMENTS

| | | | | |
|---|---|---|---|---|
| 5,517,990 A | * | 5/1996 | Kalfas et al. ................ | 600/414 |
| 5,904,691 A | * | 5/1999 | Barnett et al. ............... | 606/130 |
| 5,921,992 A | | 7/1999 | Costales et al. | |
| 5,987,960 A | * | 11/1999 | Messner et al. ............. | 73/1.79 |
| 6,021,343 A | | 2/2000 | Foley et al. | |
| 6,112,113 A | | 8/2000 | Van Der Brug et al. | |
| 6,226,548 B1 | * | 5/2001 | Foley et al. ................. | 600/426 |
| 6,228,089 B1 | * | 5/2001 | Wahrburg ..................... | 606/86 |
| 6,306,126 B1 | * | 10/2001 | Moctezuma ................... | 606/1 |
| 6,377,839 B1 | * | 4/2002 | Kalfas et al. ................ | 600/426 |
| 6,477,400 B1 | * | 11/2002 | Barrick ........................ | 600/426 |
| 7,043,961 B2 | | 5/2006 | Pandey et al. | |
| 2001/0034530 A1 | | 10/2001 | Malachowski et al. | |
| 2003/0209096 A1 | * | 11/2003 | Pandey et al. ............. | 73/865.9 |
| 2004/0054489 A1 | * | 3/2004 | Moctezuma De La Barrera et al. .......................... | 702/105 |

FOREIGN PATENT DOCUMENTS

| | | |
|---|---|---|
| WO | 96/11624 | 4/1996 |
| WO | 01/67979 | 9/2001 |

* cited by examiner

*Primary Examiner*—Samuel G. Gilbert
(74) *Attorney, Agent, or Firm*—Renner, Otto, Boisselle and Sklar, LLP

(57) ABSTRACT

A method for calibrating or registering a medical instrument or implant includes determining a spatial position of the instrument or implant and determining a relative position of the instrument or implant with respect to anatomical data. A spatial orientation of a multi-dimensionally formed, functional section of the instrument or implant is determined. A device for calibrating or registering a medical instrument or implant using a medical navigation system includes calibration aid, where the calibration aid includes a calibration section whose spatial orientation in said navigation system is known and on which a multi-dimensionally formed, functional section of the instrument or implant can be oriented.

8 Claims, 3 Drawing Sheets

NAVIGATION-CALIBRATING ROTATIONALLY ASYMMETRICAL MEDICAL INSTRUMENTS OR IMPLANTS

RELATED APPLICATION DATA

This application claims priority of U.S. Provisional Application No. 60/437,534, filed on Dec. 31, 2002, which is incorporated herein by reference in its entirety.

FIELD OF THE INVENTION

The present invention relates to navigation-calibrating rotationally asymmetrical medical instruments or implants.

BACKGROUND OF THE INVENTION

Modern, computer-assisted surgery is able, during an operation, to display a surgeon's instruments or implants on a monitor in relation to anatomical data obtained beforehand from a patient scan (e.g., CT or MR scans). To this end, the instruments and/or implants have to be calibrated. For example, the spatial position and/or the position of the functional section, for example, the tip of an instrument, in the medical navigation system being used has to be known. One option is to perform pre-calibration (pre-operative calibration), i.e., disclosing the geometric data of the instrument or implant to the navigation system in advance and storing the data securely on the software side. Another option is so-called intra-operative calibration, in which the instrument or implant is calibrated during the operation by the staff carrying out the treatment.

Using pre-operatively calibrated instruments or implants nonetheless makes it necessary in many cases to intra-operatively verify the accuracy of the instruments and re-calibrate them. In contrast, the use of intra-operative calibration makes it possible to fall back on available instruments, without being reliant on those instruments whose geometry has already been stored on the software side. In other words, each surgeon can, for example, use his own instruments. Intra-operative calibration is advantageous when instruments have changed between two operations (e.g., by re-sharpening an instrument) but have to be highly accurately calibrated during the operation.

Intra-operative calibration be performed in various ways. In one conventional calibration method, only so-called point calibration is performed, where only the length of the instrument or implant is determined, and not its geometry. A second and continuative conventional method involves determining, alongside the length, the exact vector of the instrument, i.e., its geometry, as well. Various methods and aids are used in this respect. However, each of these methods and aids are currently limited to rotationally symmetrical instruments, which are very easy to calibrate. With regard to such techniques, reference is made to U.S. Pat. No. 6,021,343, WO 96/11624 and U.S. Pat. No. 5,921,992. With these techniques, in order for the instrument to be calibrated, it must be clamped or otherwise inserted, either during the operation or shortly before the instrument is used, into a fixed calibration tool, i.e., into a means that is fixed positionally and with respect to the patient.

The disadvantage of the system described in U.S. Pat. No. 5,921,992 is again that calibration is only performed with respect to the orientation of the instrument and its punctiform tip. The system is limited in that only instruments that are suitable to being calibrated are those in which the position of the tip of the instrument and the subsequently linearly running section are important to the treatment.

SUMMARY OF THE INVENTION

It is an object of the present invention to enable instruments and implants, which are rotationally asymmetrical and/or have a substantially punctiform tip, to be calibrated. It is intended to enable complex-design instruments and implants to be calibrated, in order that they can be optimally used in the context of medical treatment.

In accordance with one aspect of the present invention, the method for calibrating or registering medical instruments or implants includes determining a spatial position of the instrument or implant by means of a medical navigation system, in order to determine the relative position of the instrument or implant with respect to anatomical data. Since, in the case of complex-design instruments and implants, information about the position of a tip or a single represented spatial orientation is not sufficient to optimally integrate the instrument or implant into the navigation, the spatial orientation of a multi-dimensionally formed, functional section of the instrument or implant is determined. In other words, the instrument is multi-dimensionally calibrated. For example, the position of a plane or an edge of the instrument is determined, if it is of a functional nature, i.e., if the function of the instrument or implant depends on how this plane or edge is spatially arranged.

Calibration in accordance with the invention may also be described as calibrating rotationally asymmetrical instruments or implants, and one advantage of the invention is based on the fact that it enables such instruments or implants to be optimally navigated, which also improves the end result, for example, creating a correct cutting plane using an instrument or correctly inserting an implant. Using the present invention, it thus becomes possible to also calibrate more complex-design instruments and implants intra-operatively, and therefore to also enable computer-assisted navigation to be used in this respect.

In accordance with one embodiment of the invention, the spatial orientation of a linear, functional section of the instrument or implant is determined. For example, if a surgical chisel is to be used as the instrument, it is advantageous to determine the spatial orientation of the cutting area of said chisel.

In accordance with another embodiment of the invention, a suitable section of the instrument or implant can be oriented on a calibration section of a calibration aid, whose spatial orientation in the navigation system is known and tracked. It can be the functional section itself that is oriented on the calibration aid or its calibration section, wherein the calibration section can exhibit a linear form, such as a linear groove. The cutting area of a surgical chisel can, for example, be oriented in such a linear groove. The calibration section can also be a plane on the calibration aid within the framework of the present invention.

In accordance with another embodiment of the invention, the spatial orientation of the multi-dimensionally formed, functional section of the instrument or implant can be determined with the aid of information already available on the orientation of another particular characteristic line or plane of the instrument or implant.

In addition, it is possible to determine the spatial orientation of the multi-dimensionally formed, functional section of the instrument or implant with the aid of registering a number of points on the instrument or implant using an already calibrated registering instrument.

In accordance with another aspect of the invention, a device for calibrating or registering medical instruments or implants can include a medical navigation system and a calibration aid. The calibration aid can include a calibration section, whose spatial orientation in the navigation system is known and on which a multi-dimensionally formed, functional section of the instrument or implant can be orientated.

In one embodiment, the calibration section is one which exhibits a linear form, such as the form of a linear groove. Alternatively, a planar calibration section is provided.

BRIEF DESCRIPTION OF THE DRAWINGS

The invention will now be illustrated in more detail by way of preferred exemplary embodiments, wherein.

DETAILED DESCRIPTION OF THE INVENTION

Figure 1:
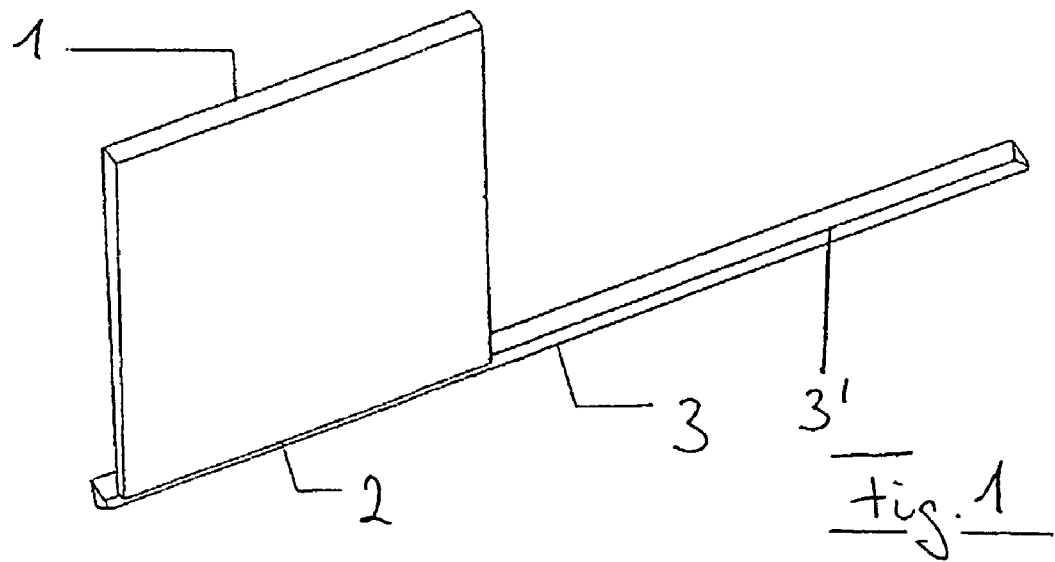
FIG. 1 is a schematic illustration of a calibration instrument for calibrating a surgical chisel in accordance with the present invention.

FIG. 1 illustrates calibration of the spatial orientation of the cutting area of a surgical chisel in accordance with one embodiment of the invention. The chisel 1 can include a cutting edge 2. If, for example, a bone structure is to be cut through using only the chisel 1, then it can be important for the parting area of the chisel 1 to have a particular orientation, such as when specific devices are to be attached to the parting area, whose orientation is also important. Therefore, it is desirable, within the context of navigation, to know the orientation of the cutting edge 2.

Within the framework of calibrating, the orientation may, for example, be determined in this way by inserting the chisel 1 via its cutting edge 2 into a groove 3' of a groove-shaped calibration instrument 3, as shown in FIG. 1. The cutting edge 2 of the chisel is thus aligned or scanned with the aid of the already known geometry of the groove 3'. This information is stored and enables the chisel 1 to be displayed during an operation, with the aid of a navigation system. Navigation systems are well known and include those described in co-owned U.S. Pat. No. 6,351,659, which is hereby incorporated by reference in its entirety. The position of the groove 3', which is known in the computer of the navigation system, can be transferred onto the instrument to be calibrated as a geometric data set.

Figure 2:
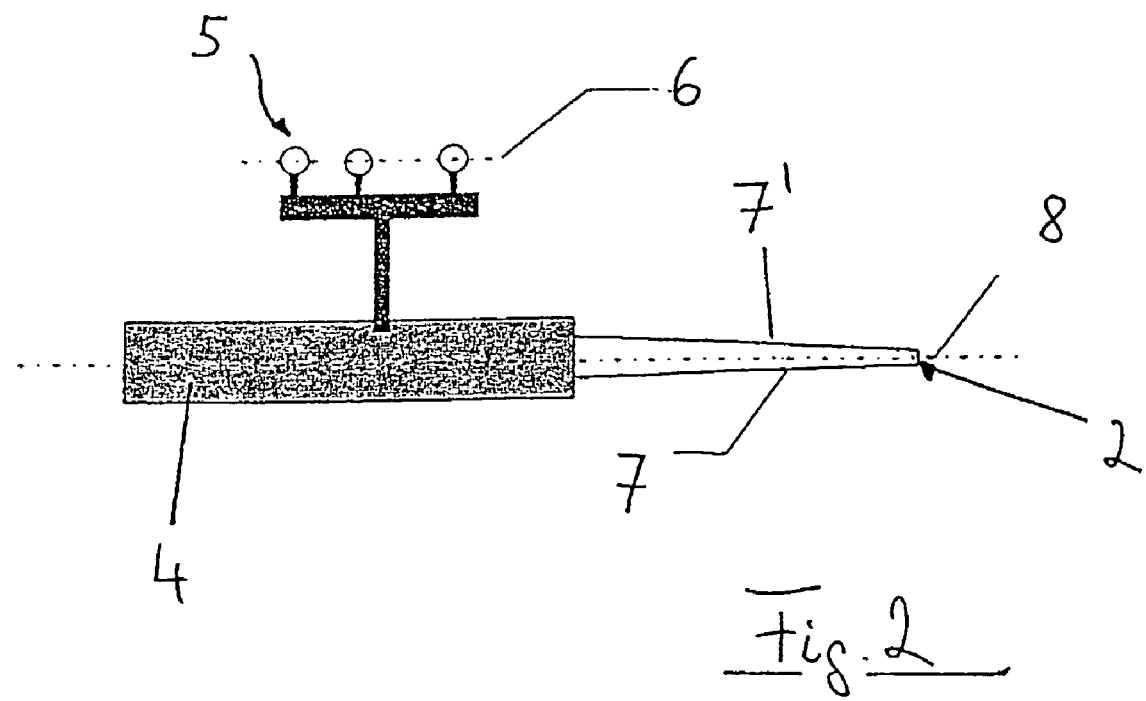
FIG. 2 is a schematic illustration of a calibration instrument for calibrating a surgical chisel in accordance with another embodiment of the present invention.

With reference now to FIG. 2, another embodiment of intra-operatively calibrating an instrument is illustrated. In this embodiment, a chisel 4 includes a blade 7 having a cutting edge 2. The plane in which the cutting edge 2 lies is indicated by the reference numeral 8. A navigational reference 5, such as, for example, a referencing adaptor comprising three reflectors, is arranged on the chisel 4. In this arrangement, the position of the referencing adaptor 5 within the navigation system may be determined via cameras associated with the navigation system. A plane 6 associated with the referencing adaptor 5, which is oriented parallel to the plane 8, may also be determined.

If the plane 6 spanned by the reflectors of the referencing adaptor 5 is then attached parallel to and at a known distance from the plane 8, then it is possible to determine or calibrate the position of an oblique area of the blade 7 and of its mirrored area 7', for example, by positioning the oblique area of the blade 7 on a known plane. The reflector plane 6 is shifted towards the plane 8 by calculation, and the straight cutting line including the plane in which the cutting edge 2 determined beforehand (e.g., as shown in FIG. 1) lies is calculated. By reflection in the plane 8, the mirrored oblique area 7' may also be calibrated. In an alternative embodiment, non-coplanar reflectors can be employed.

The geometry of the chisel can then be calculated in relation to anatomical data by the computer of the navigation system and displayed on an image output.

Figure 3:
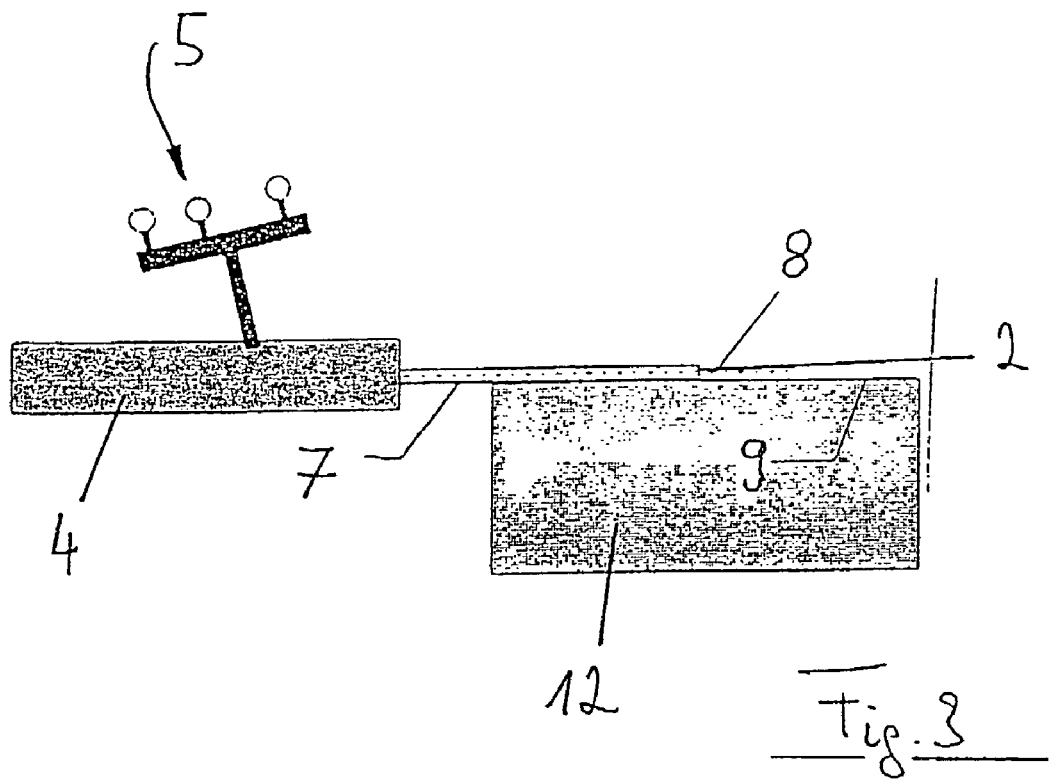
FIG. 3 is a schematic illustration of a calibration instrument for calibrating a surgical chisel in accordance with another embodiment of the present invention.

With reference now to FIG. 3, in another embodiment, a calibration tool 12 is used to determine the spatial geometry of the chisel 4 and, in particular, of its cutting edge 2. The navigational reference 5 is not primarily needed here, and is, therefore, shown in a slanted position. The calibration tool 12 includes a plane 9 whose spatial position is known. In other words, the spatial geometry of the chisel 4 can be determined with the aid of a known plane 9 outside the chisel 4. Once the chisel 4 has been oriented, such as when the cutting edge 2 has been positioned on the known plane 9, the position of the plane 8, which contains the cutting edge 2, can be determined. It is noted that the spatial orientation of the cutting edge 2 can be determined, for example, as is described with reference to FIG. 1.

Figure 4:
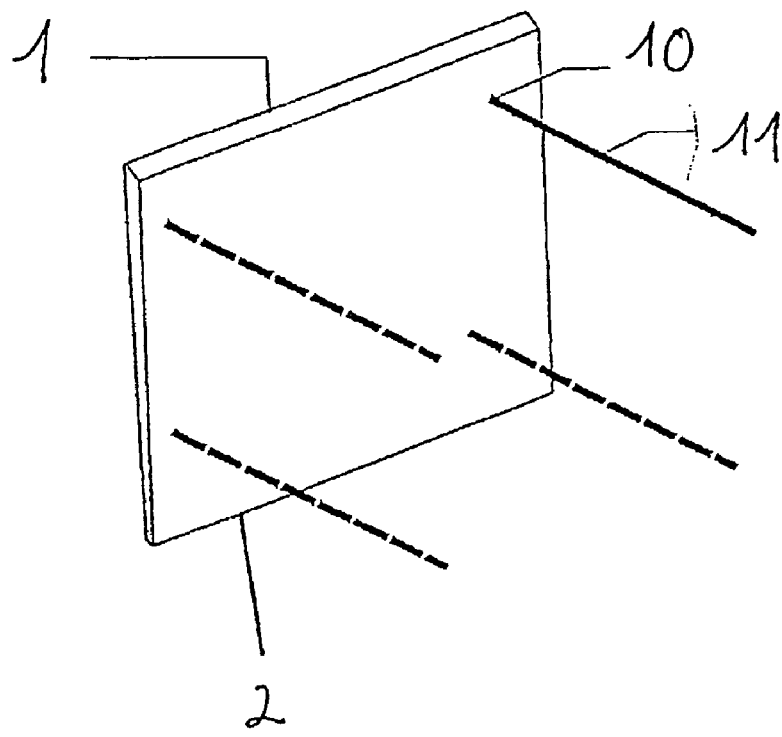
FIG. 4 is a schematic illustration of calibration of a surgical chisel with the aid of an already registered instrument in accordance with the present invention.

In another embodiment, shown in FIG. 4, the spatial orientation of the chisel 1 can be determined by a scanning method. Here, the geometry of an instrument, for example, a pointer 11, is already known to the navigation system. This information is then used to calibrate the chisel 1 and its cutting edge 2. To this end, the pointer 11 can be moved via its tip to indeterminate points of the chisel 1 or to points of the chisel 1 determined beforehand. Such a point of contact between the tip of the pointer 11 and the chisel is indicated in FIG. 4 by the reference numeral 10. The broken lines indicate that the pointer 11 can also be moved to other points.

Since the pointer 11 has already been calibrated in advance, and the position in the navigation system of its tip is therefore always known, the points traveled to are identified by the navigation system and used to determine the spatial orientation of the chisel and to store it as a reference point for navigation. Within the context of navigation, this known spatial orientation of the chisel 1 can then be displayed with respect to other information (for example, the anatomy of the patient).

Figure 5:
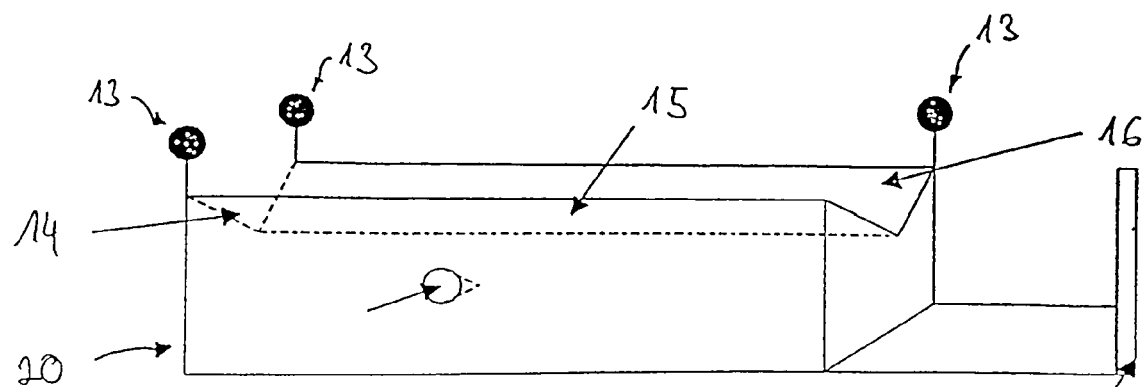
FIGS. 5–7 are schematic illustrations of functional portions of a calibration instrument for use in conjunction with the calibration of a surgical chisel in accordance with the present invention.
Figure 6:
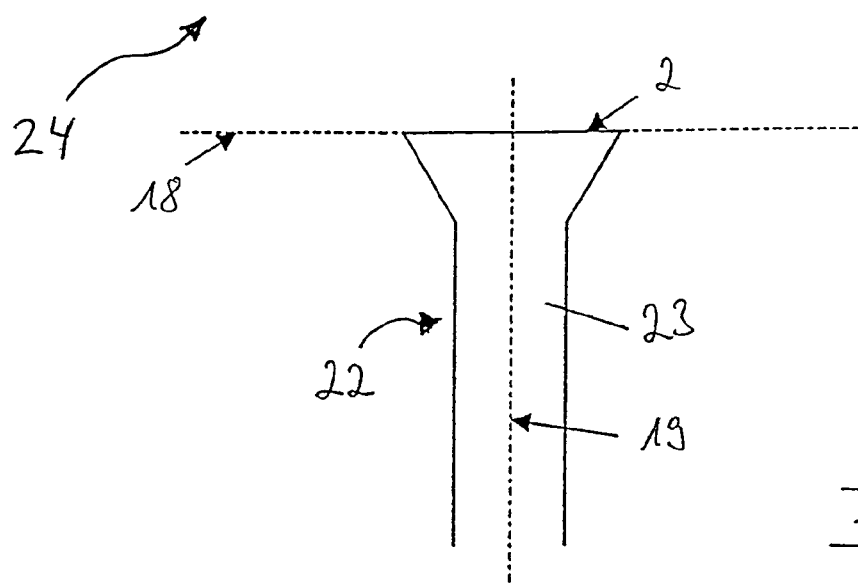
Figure 7:
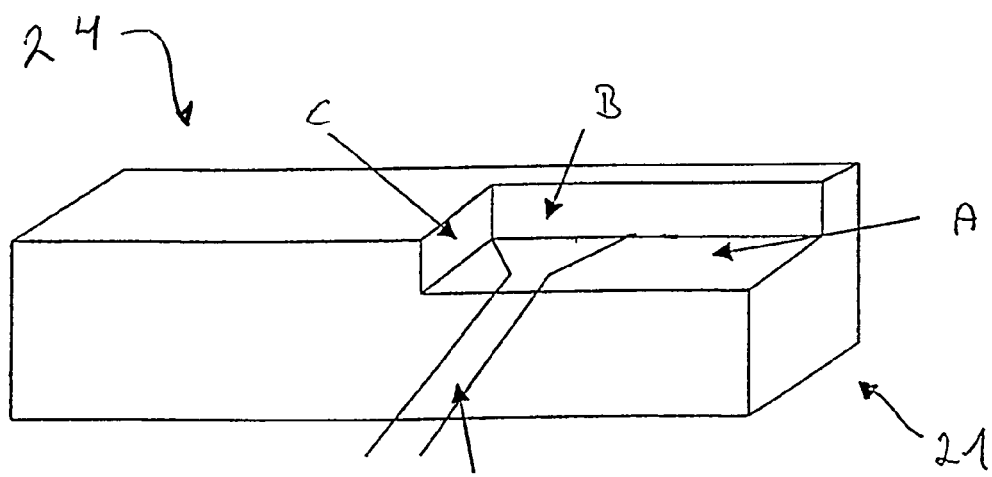

With reference now to FIGS. 5–7, an exemplary calibration is provided. FIG. 5 shows a functional portion of a calibration instrument 24 in accordance with the invention, the portion being indicated by the reference numeral 20. Another portion of the calibration instrument 24, which can similarly be provided together with the portion 20, is shown in FIG. 7 and provided with the reference numeral 21.

The instrument portion 20 includes a V-groove 14 defined by groove planes 15 and 16. In addition, a stopper 17 is also provided on the right-hand side of the instrument portion 20.

Using this calibration instrument 24 or instrument portions 20 and 21 (FIGS. 5 and 7), a chisel 22, shown in FIG. 6, may then be calibrated. The chisel includes a cutting edge 2, which lies on the edge vector 18 (also referred to as a tip vector), and a grip section 23 having an axis vector 19.

The portion 21 of the calibration instrument 24 shown in FIG. 7 includes a recess, defined by the planes A, B and C, as a functional element. Plane A is lowered parallel with respect to a top surface, and planes B and C are perpendicular to plane A and to each other. The chisel 22 is also shown in outline.

As far as calibrating the spatial orientation of the cutting edge 2 of the chisel 22 is concerned, the calibration instrument portions 20, 21 may also be used in accordance with the principle described by way of FIG. 1. In one embodiment, the cutting edge 2 of the chisel 22 can be inserted into a groove whose spatial orientation is known, for example, into the groove 14 of the instrument portion 20 or into the intersection line of planes A and B of the instrument portion 21, whose position is likewise known (for example, via reflector arrays (not shown)). The cutting edge 2 of the chisel 22 is thus positioned exactly in the groove 14 or on the edge between plane A and plane B, and geometric data on the calibration instrument are used for calibration. This presupposes that the chisel is correctly positioned relative to the calibration instrument portions 20, 21.

The spatial orientation of the cutting edge 2 can also be calibrated on one plane only, if the orientation of this plane is known, for example, that of plane B in FIG. 7. The chisel 22, which can include a tracked referencing means (such as a reflector array) on its grip section, is placed onto some point on plane B via the cutting edge 2, and rotationally moved about the cutting edge 2. Through the rotational movement, the rotational axis (i.e., the cutting edge 2) can be determined in the navigation system as an axis of rotation and calculated in its spatial orientation.

It is also possible to combine the two ways of calibrating the spatial orientation of the cutting edge 2 cited above. Due to the resultant redundancy, a plausibility check is possible. Therefore, the rotational axis can be calculated and aligned with the position determined by the groove arrangement. Given approximately correct positioning (keeping to a threshold value), the geometric data on the calibration instrument are used for calibration.

In one embodiment, intersecting planes can be calibrated when a chisel, such as that shown in FIG. 2, includes oblique areas, which can also be referred to as intersecting planes. It is to be determined here how the intersecting planes lie and at what angle they intersect.

The calibration shown in FIG. 4 offers a first approach to solving this problem in which, generally speaking, points from both planes of the chisel 1 are recorded and fitted into scatter-plot planes, using a pointed aid 11 whose geometric data are known.

With reference again to FIG. 7, in another embodiment, the intersecting planes can be positioned on planes of the calibration instrument. In two successive calibration steps, the chisel 22 can be positioned via its intersecting planes of the cutting edge 2 onto one of the planes, for example, plane A. Each intersecting plane of the cutting edge 2 can be calibrated using the known geometric data of the calibration instrument, such as plane A. If the intersecting planes of the cutting edge 2 lie at a very acute angle with respect to each other (e.g., an infinitely thin chisel), then it may be sufficient to calibrate one intersecting plane.

It is also possible, when a chisel is used together with a reference means in the navigation system, to calibrate both intersecting planes in a single step. This applies when the plane spanned by the navigational reference lies parallel to and at a known distance from the chisel axis vector 19 (FIG. 6). It is then sufficient to shift the plane of the navigational reference as far as the center of the chisel grip and to calculate the straight cutting line together with the plane of the calibration instrument (for example, plane A). By reflection in the center plane (shifted reference plane), the other intersecting plane is then also calibrated.

Other characteristics of an exemplary chisel, such as the width of its cutting edge 2 can also be calibrated in accordance with the invention. As described above, the intersecting planes of a chisel can be determined by positioning them twice on plane A at their angle to each other. In addition, there exists the possibility of also determining the width of the cutting edge 2 at the same time, if, as shown in FIG. 7, the cutting edge 2 is simultaneously positioned abutting plane C. Positioning the chisel twice, by flipping the chisel over along its longitudinal center line, allows the width of the chisel or the position of the axis vector 19 of the grip piece 23 to be calculated.

Referring again to FIGS. 5 and 6, in another embodiment, it is possible to calibrate the chisel grip 23 using the V-groove 14 on the instrument portion 20. The axis vector 19 and the radius of the chisel grip 23 section are calibrated by being inserted into the V-groove 14 and continuously rotated about the rotational axis of the chisel 22. A navigational reference (such as reflector array 13) attached fixedly to the instrument continuously provides data (samples) to the tracking or navigation system. Using computer-assisted graphic processing, these data are matched onto a cylinder. Such techniques are more fully described in co-owned U.S. Pat. No. 6,351,659, which is incorporated herein by reference in its entirety. In other words, as the chisel grip 23 is rotated, the reflectors 13 each define a cylinder whose axis coincides with the axis 22 of the chisel grip 23. The spacing of the axis 22 from the walls of the V-groove 14 provide the radius of the chisel grip 23. It is important to track the grip 23 in order to avoid interference with sensitive anatomical areas. In one embodiment, an alarm may sound if interference with sensitive anatomical areas is imminent.

The chisel grip 23 initially has a random radius. Its axis, however, lies parallel to the V-groove 14 and on a plane spanned by the V-groove 14 and a vector lying perpendicular to the V-groove and bisecting an aperture angle of the V-groove. Once calculations are completed with error correction (for example, smallest quadratic error, standard deviation as a plausibility check), then the initially variable radius of the chisel grip 23 is the calibrated radius of the rotationally symmetrical portion. This facilitates checking for errors that may occur if the chisel grip 23 is not fully seated in the V-groove 14. In the event of inaccurate calibration, the accuracy of calibration can be increased by matching the chisel grip 23 again with the aid of a manually inputted radius.

If the chisel grip 23 has then been calibrated, the chisel cutting edge 2 width can be calibrated by means of the technique already described above, i.e. with the aid of a lateral abutment (plane C in FIG. 7), wherein only one side of the cutting edge has to abut plane C since the axis vector 19 is known. With the above step, all necessary calibration on the instrument has then been performed.

With reference to FIGS. 2 and 6, in another embodiment, calibrating a chisel (the spatial orientation of the cutting area 2 and calibrating the grip 23) can occur in a single calibration step. If it can be ensured that a plane (for example, plane 6 in FIG. 2) spanned by a navigational reference 5 (e.g., reflector adaptor) lies parallel to the vector 8, 18 of the cutting area 2, then individually calibrating the spatial orientation of the cutting edge can be omitted. Then, as described last above, the axis vector 19 of the grip 23 has to be calibrated in combination with length, which is, for example, possible by using the stopper 17 (shown in FIG. 5). The spatial position and orientation of the edge vector 18 are then calculated using the given parallelism to the plane 6 spanned by the navigational reference 5 and from the axis vector 19 of the instrument, which intersects the edge vector 18 at a perpendicular angle. The length of the cutting area 2 is then either inputted manually or determined by positioning on the boundary plane C (FIG. 7) as described above.

Although particular embodiments of the invention have been described in detail, it is understood that the invention is not limited correspondingly in scope, but includes all changes, modifications and equivalents coming within the spirit and terms of the claims appended hereto.

What is claimed is:

1. A device for calibrating or registering a rotationally asymmetrical medical instrument or implant using a medical navigation system, said device comprising:
    a calibration aid, said calibration aid including:
        a first calibration section whose spatial orientation is known in or determinable by the navigation system, said first calibration section comprising a recess defined by at least three planes and being operative to accept a multi-dimensionally formed, functional section of the instrument or implant to calibrate said instrument; and
        a second calibration section whose spatial orientation is known in or determinable by the navigation system, said second calibration section comprising a recess defined by at least two planes, wherein said second calibration section is operative to accept the multi-dimensionally formed, functional section of the instrument or implant to calibrate said instrument.

2. A system for calibrating or registering a rotationally asymmetrical medical instrument or implant, comprising:
    the device of claim 1; and
    a medical navigation system operative to determine the spatial orientation of the first and/or second calibration section.

3. The device as set forth in claim 1, wherein determining the spatial orientation includes determining the spatial orientation of the functional section of the instrument or implant.

4. The device as set forth in claim 3, wherein the instrument is a surgical chisel and the functional section is a cutting edge of the surgical chisel.

5. The device as set forth in claim 1, wherein the second calibration section is in the form of a linear groove.

6. The device as set forth in claim 1, wherein the first calibration section includes a plurality of boundary planes.

7. The device as set forth in claim 6, wherein the plurality of boundary planes include a plurality of intersecting lines or intersecting points enclosed thereby.

8. A method for calibrating or registering a rotationally asymmetrical medical instrument or implant, wherein a spatial position of said instrument or implant is determined or tracked so as to enable a relative position of said instrument or implant to be shown in relation to anatomical data, said method comprising:
    rotating the instrument about a functional section of the instrument while maintaining the functional section on a plane;
    determining a rotational axis of the instrument; and
    calculating a spatial orientation of the instrument based the axis of rotation.

* * * * *